US007722546B2

(12) United States Patent
Madaus et al.

(10) Patent No.: US 7,722,546 B2
(45) Date of Patent: May 25, 2010

(54) METHOD AND DEVICE FOR CARRYING OUT A SIGNAL-PROCESSING VIEWING OF A MEASUREMENT SIGNAL THAT IS CORRELATED TO THE RESPIRATORY ACTIVITY OF AN INDIVIDUAL

(75) Inventors: Stefan Madaus, Krailing (DE); Jorg Meier, Munich (DE); Dieter Heidmann, Gerelsried (DE); Hartmut Schneider, Lutherville, MD (US)

(73) Assignee: Map Medizin-Technologie GmbH, Martinsried (DE)

( * ) Notice: Subject to any disclaimer, the term of this patent is extended or adjusted under 35 U.S.C. 154(b) by 950 days.

(21) Appl. No.: 10/531,476

(22) PCT Filed: Oct. 17, 2003

(86) PCT No.: PCT/EP03/11524

§ 371 (c)(1),
(2), (4) Date: Apr. 15, 2005

(87) PCT Pub. No.: WO2004/034938

PCT Pub. Date: Apr. 29, 2004

(65) Prior Publication Data

US 2006/0037614 A1    Feb. 23, 2006

(30) Foreign Application Priority Data

Oct. 17, 2002    (DE) ................... 102 48 590

(51) Int. Cl.
*A61B 5/08*    (2006.01)

(52) U.S. Cl. ...................... 600/538; 600/529

(58) Field of Classification Search ......... 600/529–543; 128/204.23
See application file for complete search history.

(56) References Cited

U.S. PATENT DOCUMENTS 4,777,962 A * 10/1988 Watson et al. ............... 600/529

(Continued)

FOREIGN PATENT DOCUMENTS

JP    2000-504602    4/2000

(Continued)

OTHER PUBLICATIONS

International Search Report of PCT/EP03/11524 mailed Feb. 18, 2004.

*Primary Examiner*—Patricia C Mallari
*Assistant Examiner*—Karen E Toth
(74) *Attorney, Agent, or Firm*—Nixon & Vanderhye P.C.

(57)    ABSTRACT

The invention relates to a method and device for carrying out a signal-processing viewing of a measurement signal that is correlated with the respiratory activity of an individual, for example, of a measurement signal that is correlated with the respiratory gas. The aim of the invention is to provide solutions with which an improved electronic analysis of the signals that are representative with regard to respiratory activity can be achieved. To this end, the invention provides that viewing results are obtained within the scope of a signal-processing viewing of said measurement signal and make a differentiation between obstructive and central respiratory disorders possible. The viewing results are determined, in particular, while taking into account changes of selected breathing characteristics such as, for example, the change in the ratio of inhalation time to exhalation time.

38 Claims, 2 Drawing Sheets

Figure 1:
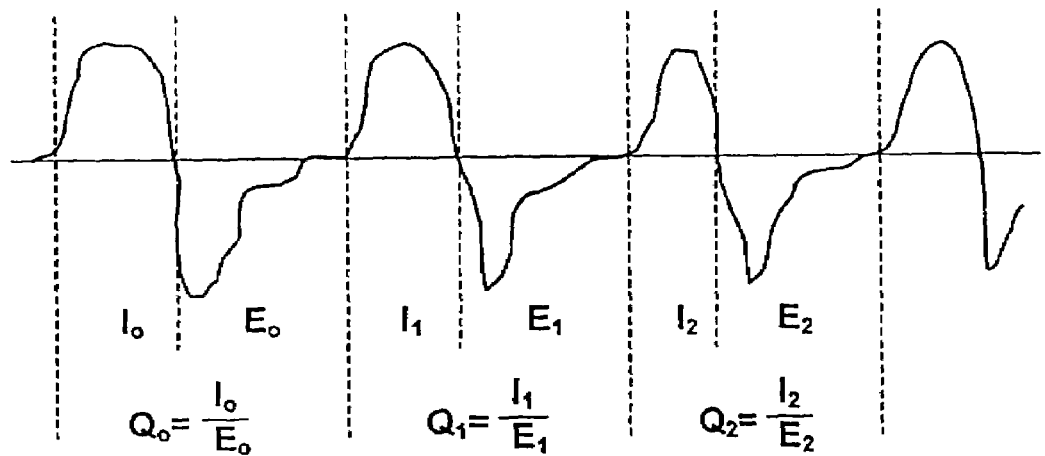

Consideration of the variation in characteristic features of the curve shape of successive inspiration cycles

U.S. PATENT DOCUMENTS

| | | | | |
|---|---|---|---|---|
| 5,146,918 | A * | 9/1992 | Kallok et al. | 607/2 |
| 5,335,654 | A * | 8/1994 | Rapoport | 128/204.23 |
| 5,704,345 | A * | 1/1998 | Berthon-Jones | 128/204.23 |
| 5,803,066 | A | 9/1998 | Norman et al. | |
| 6,015,388 | A * | 1/2000 | Sackner et al. | 600/529 |
| 6,029,665 | A * | 2/2000 | Berthon-Jones | 128/204.23 |
| 6,085,747 | A * | 7/2000 | Axe et al. | 128/204.23 |
| 6,105,575 | A | 8/2000 | Mechlenburg et al. | |
| 6,165,133 | A * | 12/2000 | Rapoport et al. | 600/529 |
| 6,287,264 | B1 * | 9/2001 | Hoffman | 600/538 |
| 6,363,933 | B1 | 4/2002 | Berthon-Jones | |
| 6,530,372 | B1 * | 3/2003 | Madaus et al. | 128/204.23 |
| 6,651,652 | B1 * | 11/2003 | Wård | 128/200.24 |
| 6,739,335 | B1 * | 5/2004 | Rapport et al. | 128/204.18 |
| 6,752,151 | B2 * | 6/2004 | Hill | 128/204.18 |
| 6,814,074 | B1 * | 11/2004 | Nadjafizadeh et al. | 128/204.23 |
| 2002/0043264 | A1 * | 4/2002 | Wickham | 128/204.18 |
| 2003/0045806 | A1 * | 3/2003 | Brydon | 600/534 |
| 2004/0230105 | A1 * | 11/2004 | Geva et al. | 600/301 |
| 2006/0037615 | A1 * | 2/2006 | Wilkinson et al. | 128/204.23 |
| 2007/0150022 | A1 * | 6/2007 | Ujhazy et al. | 607/42 |

FOREIGN PATENT DOCUMENTS

| | | |
|---|---|---|
| JP | 2002-505924 | 2/2002 |
| WO | WO 97/28838 | 8/1997 |
| WO | WO 99/45989 | 9/1999 |
| WO | 02 47747 A | 6/2002 |
| WO | 03 059158 A | 7/2003 |

* cited by examiner

Consideration of the inspiration/expiration ratio

Consideration of the variation in characteristic features of the curve shape of successive inspiration cycles Consideration of the changes in curve shape features for successive expiration cycles Interval 0   Interval 1   Interval 2   Interval 3

Consideration of the variation in curve shape features in an interval within successive inspiration cycles - Consideration of the variation in the lengths of defined intervals in successive inspiration cycles

METHOD AND DEVICE FOR CARRYING OUT A SIGNAL-PROCESSING VIEWING OF A MEASUREMENT SIGNAL THAT IS CORRELATED TO THE RESPIRATORY ACTIVITY OF AN INDIVIDUAL

This application is the US national phase of international application PCT/EP2003/011524 filed 17 Oct. 2003, which designated the U.S. and claims priority of DE 102 48 590.9, filed 17 Oct. 2002, the entire contents of each of which are hereby incorporated by reference.

The invention concerns a method of and an apparatus for carrying out signal-processing consideration of a measurement signal related to respiration activity, for example the respiratory gas flow, in particular for matching pressure regulation in the administration of a breathable gas at a pressure level which at least in phase-wise manner is above the ambient pressure, and generally for the diagnosis and/or therapy of sleep-related breathing disorders.

To treat sleep-related breathing disorders it is known to supply a patient with a respiratory gas, in particular ambient air, at a pressure level which is above the ambient pressure level at least in phase-wise manner. The administration of the respiratory gas at an increased pressure level makes it possible to implement pneumatic splinting in the region of the upper respiratory tracts, whereby it is possible to preclude any obstructions in that respiratory tract region in a physiologically highly compatible fashion.

Particularly good compatibility of the supply of the respiratory gas at an elevated pressure level is achieved if the respiratory gas pressure is set to a pressure which is as low as possible and which is only sufficient for obstruction prevention or obstruction limitation. It is known to implement setting of the instantaneously required respiratory gas pressure, having regard to the evaluation results of signal-processing consideration of the instantaneous respiratory gas flow, by means of an electronic pressure regulating device which is integrated into a CPAP unit. The instantaneous respiratory gas flow can be detected in particular by volume flow sensors, for example measurement orifices.

In the case of CPAP units with automatic pressure matching the electronic pressure regulating device is configured with the aim that the respiratory gas pressure required is afforded with an adequate level of certainty, but on the other hand the dynamics of the variation in pressure are so slight that the sleep pattern of the patient is not noticeably adversely affected by the changes in the respiratory gas pressure. Adverse effects can occur in particular if comparatively high respiratory gas pressure levels are temporarily set.

The object of the present invention is to provide ways with which it is possible to achieve electronic evaluation, which is accurate with a high degree of probability, of a signal that is representative in respect of respiration activity, so that, based on that evaluation, the physiological state of a patient can be accurately determined and/or the respiratory gas supply, in particular the respiratory gas pressure, can be matched to the instantaneous physiological demands in an improved manner.

In accordance with the invention that object is attained in that, in the context of signal-processing consideration of a measurement signal which is indicative of the respiratory gas flow, consideration results are obtained which permit differentiation between obstructive and central breathing disorders.

In that way it is advantageously possible, in connection with detection of the instantaneous respiratory gas flow, to implement an analysis of trends, by virtue of which it is possible to carry out the measures which are most suitable for eliminating or preventing an instantaneous or impending breathing disorder, in particular involving matching the pressure regulating characteristics.

In accordance with a particularly preferred embodiment of the invention signal-processing consideration is effected in such a way that the inspiration time and the expiration time for successive breaths is detected thereby. By determining the ratio of the inspiration time and the expiration time and by considering the variation in respect of time of those ratios, it is possible to recognise a trend as to whether imminent breathing disorders or breathing disorders which already exist are caused obstructively and/or centrally.

In particular in combination with that measure, or also alternatively thereto, it is also possible to obtain information in respect of an existing or imminent disorder phase from comparative consideration of successively occurring changes in properties of the derivatives and in particular the first derivative of the respiratory gas flow in the region of the breathing phase change.

The ratio of inspiration time Ix to expiration time Ex can be used to describe breathing disorders. In particular a trend in the variation in the duration of the inspiration time with respect to the expiration time can give an indication of an imminent obstruction in the upper respiratory tracts. Furthermore, consideration of the ratio of inspiration time Ix to expiration time Ex in a trend analysis procedure can contribute to distinguishing obstructive from central apneas.

Exact measurement of the respiratory gas flow 'flow curve' is particularly advantageous.

The ratio of inspiration to expiration can be referred to as the duty cycle and represents an information carrier for assessment of the respiratory flow disturbances in the upper respiratory tracts. If flow limitations actually occur, the inspiration time seemingly increases. The nasally measured resistance of the upper respiratory tracts in contrast remains unchanged. If it is assumed that the breathing minute volume remains constant, it is possible to deduce a relationship between the volume flow, the inspiration duration and the breath duration. (The breath minute volume is equal to the volume flow multiplied by the inspiration time and divided by the breath duration.)

In particular in combination with that measure or also alternatively thereto it is also possible to obtain information for an existing or imminent disturbance phase from comparative consideration of successively occurring changes in properties of the derivatives of the—or within the—respiratory cycles, in particular the first derivative of the respiratory gas flow in the region of the breathing phase change.

Consideration of the differential can be directed to the beginning of the inspiration cycle and/or to the end of the inspiration cycle and also to consideration of the curve shape during the inspiration cycle.

The average gradient can be calculated in simple form for intervals which extend for example over 10% of the time duration of the respective breathing phase.

The gradient (for example the maximum gradient at the phase change) can also be calculated floatingly within a window over the inspiration cycle.

The trend analysis in particular in respect of the nature and constitution of the respiratory drive is preferably implemented having regard to/with the inclusion of the signal evaluation results set forth hereinafter:

max. peak flow during the inspiration cycle the breath volume the inspiration time, and the second derivative of the measured flow curve.

In accordance with a further aspect of the invention signal-processing consideration is effected on the basis of consideration of the differential at the beginning of the expiration cycle or at the end of the expiration cycle respectively. The differential can be calculated in a simple form over an interval of for example 10% at the beginning of the expiration cycle and after the expiratory maximum flow or computed floatingly over the expiration cycle. Evaluation can advantageously be effected in a similar fashion to that described hereinbefore, with the inclusion of the maximum peak flow during the expiration cycle, the breath volume and/or the expiration time and/or the second derivative (curvature) of the measured flow curve during the expiration cycle. The evaluation procedure also makes it possible to afford information about the nature and the constitution of the upper respiratory tracts.

The flattening of the respiratory flow curve during the inspiration cycle can be interpreted in accordance with the model of the Starling resistor as a flow limitation. Consideration of the configuration of the curve shape during the inspiration cycle in an interval between for example 10% after the beginning of the inspiration cycle and 10% before the end thereof can advantageously provide information about the elastic properties of the upper respiratory tracts. It is also possible in that way to draw a conclusion about the Pcrit-value (the pressure at which the upper respiratory tracts close).

The signal processing procedure advantageously embraces in particular analysis of the number of local maxima and minima, the amplitude of the local maxima and minima, the sequence of the magnitude of the amplitudes of local maxima and minima and the frequency involved in the sequence of the local maxima and minima.

In accordance with a further aspect of the present invention the signal processing procedure according to the invention preferably also includes spectral consideration and consideration in respect of amplitude of a snoring signal and on the basis thereof can furnish information about the nature of the elastic properties of the upper respiratory tracts and possibly about the nature and location of the closure in the upper respiratory tracts.

In accordance with a particular aspect signal-processing evaluation and the trend analysis based thereon are effected on the basis of combined consideration of at least two parameters as specified hereinafter. Trend analysis is preferably based on consideration of the variation in the ratios of the parameters when considered in combination:

- inspiration time
- expiration time
- breath duration and breath frequency
- breath volume during the inspiration cycle
- breath volume during the expiration cycle
- first differential and second differential of the respiratory flow
- amplitudes of local maxima and local minima
- frequency of local maxima and local minima
- inflexion points
- maximum inspiratory flow and maximum expiratory flow.

Signal-processing consideration of the above-specified parameters can give information about the following:

- the nature of the upper respiratory tracts inter alia for distinguishing between central and obstructive apneas
- the elastic properties of the upper respiratory tracts (restoring modulus, modulus of elasticity)
- the location of an obstruction
- the degree of severity of a sleep apnea
- the Pcrit-value.

Figure 2:
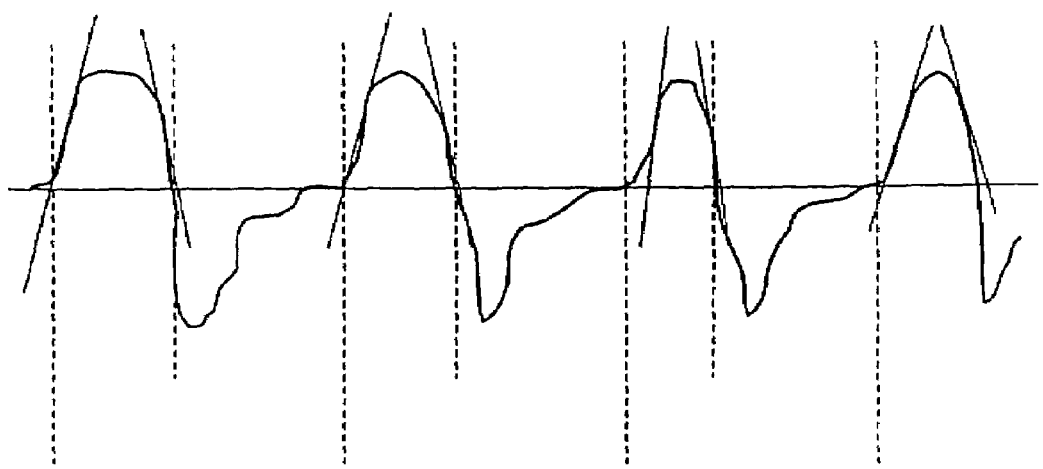
Figure 3:
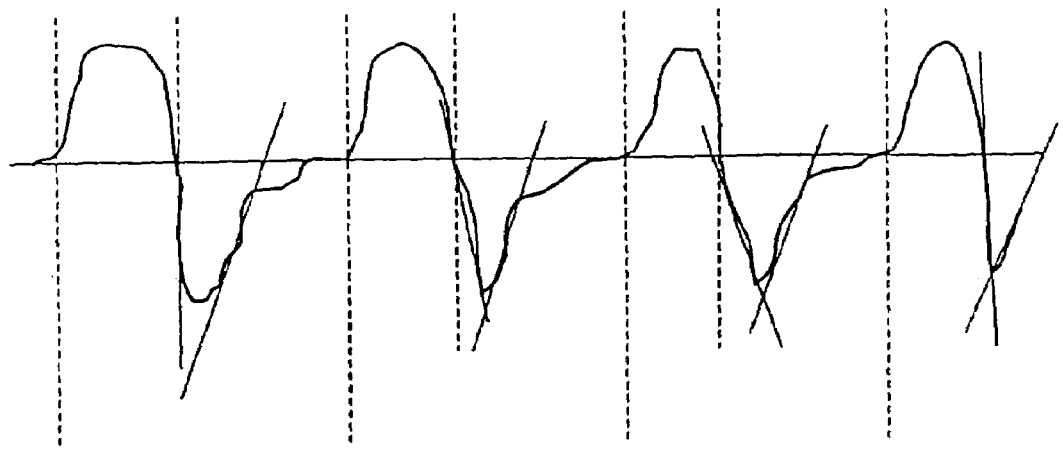
Figure 4:
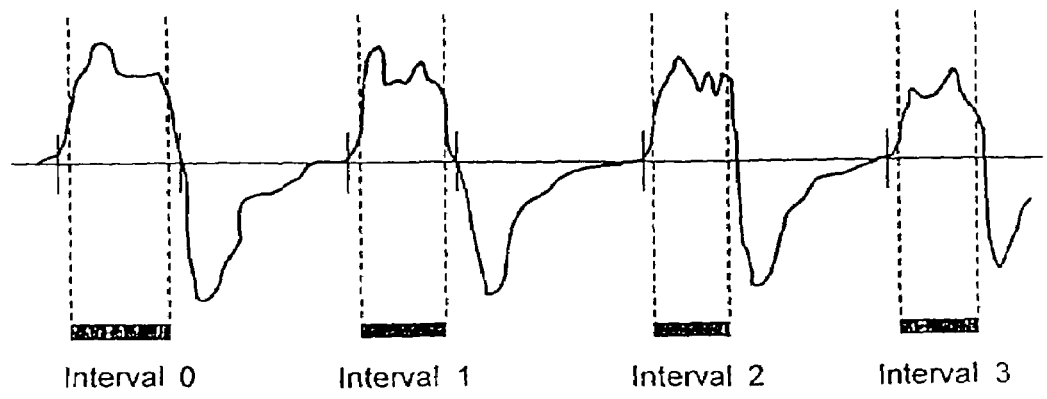

Further details and features will be apparent from the description hereinafter with reference to the drawing in which:

FIG. 1 shows a part of a respiratory gas flow chart to explain signal-processing consideration on the basis of ascertaining the ratios of the inspiration duration to the expiration duration for successive respiratory cycles, FIG. 2 shows a part of a respiratory gas flow chart to explain signal-processing consideration on the basis of consideration of the change in the curve shape features of successive inspiration cycles, FIG. 3 shows a part of a respiratory gas flow chart to explain signal-processing consideration on the basis of consideration of the change in the curve shape features of successive expiration cycles, and FIG. 4 shows a part of a respiratory gas flow chart to explain signal-processing consideration on the basis of evaluation of curve shape features within intervals in successive inspiration cycles.

FIG. 1 shows a part from a respiratory gas flow chart for explaining signal-processing consideration on the basis of ascertaining the ratios of the inspiration duration to the expiration duration for successive respiratory cycles.

The ratio of inspiration time Ix to expiration time Ex and in particular the variation thereof for successive respiratory cycles represents information which is indicative in respect of the occurrence of breathing disorders. In particular a trend in the change in the duration of the inspiration time with respect to the expiration time can give a pointer to imminent obstruction in the upper respiratory tracts. In addition consideration of the ratio of inspiration time Ix to expiration time Ex in a trend analysis can contribute to differentiating obstructive from central apneas. Measurement of the respiratory gas flow, which is as accurate as possible, and therewith possible depiction of the flow curve is advantageous.

The ratio of inspiration to expiration can be referred to as the duty cycle and represents an information carrier for assessment of the respiratory flow disturbances in the upper respiratory tracts. If flow limitations actually occur, the inspiration time seemingly increases. The nasally measured resistance of the upper respiratory tracts in contrast remains unchanged.

If it is assumed that the breathing minute volume remains constant, it is possible to deduce a relationship between the volume flow, the inspiration duration and the breath duration. (The breath minute volume is equal to the volume flow multiplied by the inspiration time and divided by the breath duration.)

FIG. 2 shows a part of a respiratory gas flow chart to explain signal-processing consideration on the basis of consideration of the change in curve shape features of successive inspiration cycles. The chart in FIG. 2 illustrates the mean gradient ascertained by way of the first derivative of the respiratory gas flow at the beginning of the inspiration cycle and at the end of the inspiration cycle respectively. That mean gradient is calculated in a simple form over for example a 10% interval or calculated floatingly over the inspiration cycle. Further curve shape features that can be taken into consideration are in particular the extreme values of the respiratory gas flow (peak flow during the inspiration cycle) and/or the breath volume and/or the inspiration time and/or the second derivative of the detected flow curve. Evaluation of those curve shape features—and in particular consideration of the variation thereof—permits information to be obtained about the nature and the constitution of the breathing drive, that is to say the instantaneous physiological state of the patient or the physiological state which prevails shortly.

FIG. 3 shows a part from a respiratory gas flow chart for explaining signal-processing consideration on the basis of consideration of the change in curve shape features of successive expiration cycles, in particular in the form of evaluation of the differential at the beginning of the expiration cycle or at the end of the expiration cycle respectively as can be ascertained in a simple form for example for a 10% interval at the beginning of the expiration cycle and after the expiratory maximum flow or floatingly over the expiration cycle.

Similarly as specified for FIG. 2, in this case also further curve shape features which can be taken into consideration are in particular the extreme values of the respiratory gas flow (peak flow during the expiration cycle) and/or the breath volume and/or the expiration time and/or the second derivative of the detected flow curve. Evaluation of those curve shape features—and in particular consideration of the variation thereof—permits information to be obtained about the nature and the constitution of the breathing drive, that is to say the instantaneous physiological state of the patient or the physiological state which prevails shortly.

FIG. 4 shows a part of a respiratory gas flow chart to explain a signal-processing consideration procedure on the basis of evaluation of curve shape features with intervals in successive inspiration cycles.

The flattening of the respiratory flow curve during the inspiration cycle can be interpreted (in accordance with the model of the Starling resistor) as a flow limitation. Consideration of the pattern of the curve shape during the inspiration cycle in an interval between for example 10% after the beginning of the inspiration cycle and 10% before the end thereof gives information for example about the elastic properties of the upper respiratory tracts.

This analysis also makes it possible to draw conclusions about the Pcrit-value (pressure at which the upper respiratory tracts close).

In carrying out a trend analysis procedure in particular the following evaluation intermediate results are advantageously taken into consideration:
  number of local maxima and minima
  the amplitude of the local maxima and minima
  the sequence of the magnitude of the amplitudes of local maxima and minima,
  the frequency in the succession of the local maxima and minima
  curve shape in an interval during the inspiration cycle length of the intervals.

Spectral consideration and consideration in respect of amplitude of a snoring signal can further provide information about the nature of the elastic properties of the upper respiratory tracts and about the location and nature of the closure in the upper respiratory tracts.

The invention is not limited to the examples of use described hereinbefore. It can be employed in particular in controlling respiratory gas pressure and matching pressure regulation in a CPAP-unit by using a suitably configured signal processing device. It can also be employed in regard to time-displaced evaluation of a series of measurement data and in that situation permits visualisation of obstructively or centrally caused phases of disturbed respiration. The invention can also be used in conjunction with a pneumotachograph generally for investigating the sleep breathing of a patient without in that respect any disturbances of obstructive nature having to be simultaneously eliminated directly by a respiratory gas supply at increased pressure.

The invention claimed is:

1. A method of carrying out signal-processing consideration of a measurement signal related to the respiration activity of a person when matching pressure regulation in administering a breathable gas at a pressure level which at least in phase-wise manner is above ambient pressure, the method comprising:
  differentiating the measurement signal on a positive airway pressure (PAP) device to generate evaluation results indicative of the respiratory gas flow, the differentiating permitting classification between obstructive and central breathing disorders,
  wherein the differentiating alone permits classification between obstructive and central breathing disorders.

2. A method as set forth in claim 1, further comprising detecting inspiration time and expiration time for successive breaths.

3. A method as set forth in claim 1, further comprising detecting a ratio of inspiration time and expiration time.

4. A method as set forth in claim 3, further comprising generating an evaluation signal which gives information as to whether imminent or already existing breathing disorders are obstructively and/or centrally caused based on the change with respect to time of said ratios.

5. A method as set forth in claim 3, wherein the evaluation results which give information as to whether a breathing disorder phase is imminent are generated from comparative evaluation of successively occurring changes in properties of the derivatives.

6. A method as set forth in claim 2, further comprising describing breathing disorders using a ratio of inspiration time Ix to expiration time Ex.

7. A method as set forth in claim 2, wherein a change in the duration of the inspiration time with respect to the expiration time is indicative of an imminent obstruction in the upper respiratory tracts.

8. A method as set forth in claim 2, further comprising extracting the evaluation results for an existing or imminent disturbance phase from comparative consideration of successively occurring changes in properties of derivatives of, or within, respiratory cycles.

9. A method as set forth in claim 2, wherein consideration is directed to the curve shape during the inspiration cycle.

10. A method as set forth in claim 9, further comprising calculating an average gradient in simple form for intervals which extend over a predetermined percentage of the time duration of the respective breathing phase.

11. A method as set forth in claim 9, further comprising variably calculating a gradient at the phase change within a window over the inspiration cycle.

12. A method as set forth in claim 1, further comprising performing trend analysis based on the nature and constitution of breathing drive.

13. A method as set forth in claim 12, further comprising performing the trend analysis based on one or more of the following signal evaluation results: max. peak flow during the inspiration cycle, the breath volume, the inspiration time, and the second derivative of the measured flow curve.

14. A method as set forth in claim 1, further comprising performing an evaluation procedure that includes consideration of the maximum peak flow during the expiration cycle, the breath volume and/or the expiration time and/or the second derivative or curvature of the measured flow curve during the expiration cycle.

15. A method as set forth in claim 14, further comprising generating, based on the evaluation procedure, an evaluation result which furnishes information about the nature and the constitution of the upper respiratory tracts.

16. A method as set forth in claim 1, further comprising performing trend analysis of the evaluation results including combined consideration of at least two parameters.

17. A method as set forth in claim 16, wherein the trend analysis is based on consideration of the variation in the ratios between two of the following parameters: inspiration time, expiration time, breath duration, breath frequency, breath volume during the inspiration cycle, breath volume during the expiration cycle, first differential and second differential of the respiratory flow, amplitudes of local maxima and local minima, frequency of local maxima and local minima, inflexion points, maximum inspiratory flow, and maximum expiratory flow.

18. An apparatus for carrying out the method as set forth in claim 1.

19. A method as set forth in claim 5, wherein the derivative is the first derivative of the respiratory gas flow in the region of the breathing phase change.

20. A method as set forth in claim 8, wherein the derivative is the first derivative of the respiratory gas flow in the region of the breathing phase change.

21. A method as set forth in claim 10, wherein the predetermined percentage is 10%.

22. A method of carrying out signal-processing consideration of a measurement signal related to the respiration activity of a person when matching pressure regulation in administering a breathable gas at a pressure level which at least in phase-wise manner is above ambient pressure, the method comprising:
   differentiating the measurement signal on a positive airway pressure (PAP) device to generate evaluation results indicative of the respiratory gas flow, the differentiating permitting classification between obstructive and central breathing disorders;
   detecting inspiration time and expiration time for successive breaths; and
   extracting the evaluation results for an existing or imminent disturbance phase from comparative consideration of successively occurring changes in properties of derivatives of, or within, respiratory cycles,
   wherein consideration of the derivatives is directed to the beginning of the inspiration cycle and/or to the end of the inspiration cycle.

23. A method of carrying out signal-processing consideration of a measurement signal related to the respiration activity of a person when matching pressure regulation in administering a breathable gas at a pressure level which at least in phase-wise manner is above ambient pressure, the method comprising:
   differentiating the measurement signal on a positive airway pressure (PAP) device to generate evaluation results indicative of the respiratory gas flow, the differentiating permitting classification between obstructive and central breathing disorders,
   wherein the signal-processing consideration is carried out based on consideration of a derivative taken at the beginning of the expiration cycle or at the end of the expiration cycle respectively.

24. A method as set forth in claim 23, further comprising calculating the derivative either (a) in a simple form over a predetermined interval at the beginning of the expiration cycle and after the expiratory maximum flow, or (b) variably over the expiration cycle.

25. A method as set forth in claim 24, wherein the predetermined interval is 10%.

26. A method of carrying out signal-processing consideration of a measurement signal related to the respiration activity of a person when matching pressure regulation in administering a breathable gas at a pressure level which at least in phase-wise manner is above ambient pressure, the method comprising:
   differentiating the measurement signal on a positive airway pressure (PAP) device to generate evaluation results indicative of the respiratory gas flow, the differentiating permitting classification between obstructive and central breathing disorders; and
   analyzing the number of local maxima and minima, the amplitude of the local maxima and minima, the sequence of the magnitude of the amplitudes of local maxima and minima, and the frequency in the sequence of local maxima and minima in considering the configuration of the curve shape.

27. A method of carrying out signal-processing consideration of a measurement signal related to the respiration activity of a person when matching pressure regulation in administering a breathable gas at a pressure level which at least in phase-wise manner is above ambient pressure, the method comprising:
   differentiating the measurement signal on a positive airway pressure (PAP) device to generate evaluation results indicative of the respiratory gas flow, the differentiating permitting classification between obstructive and central breathing disorders; and
   performing spectral consideration and consideration in respect of amplitude of a snoring signal.

28. A method of carrying out signal-processing consideration of a measurement signal related to the respiration activity of a person when matching pressure regulation in administering a breathable gas at a pressure level which at least in phase-wise manner is above ambient pressure, the method comprising:
   differentiating the measurement signal on a positive airway pressure (PAP) device to generate evaluation results indicative of the respiratory gas flow, the differentiating permitting classification between obstructive and central breathing disorders; and
   generating evaluation results based on an evaluation procedure which give information about at least one of the following:
   the nature of the upper respiratory tracts, at least for differentiating between central and obstructive apneas,
   the elastic properties of the upper respiratory tracts,
   the location of an obstruction,
   the degree of severity of a sleep apnea, and
   the Pcrit-value.

29. A method as set forth in claim 28, wherein the elastic properties of the upper respiratory tracts include restoring modulus and/or modulus of elasticity.

30. An apparatus for supplying a respiratory gas to a patient at a pressure level which is above the ambient pressure at least in phase-wise manner, comprising
   a delivery device for delivering the respiratory gas,
   a measuring device for generating a signal indicative of the respiratory gas flow,
   a regulating device for regulating the respiratory gas pressure to a predetermined reference pressure,
   a pressure presetting device for presetting the reference pressure, and
   a signal processing device configured to generate, based on a variation in respiratory cycle-specific reference features obtained via differentiation, an evaluation result which is indicative of whether or to what extent a prevailing or imminent breathing disorder is of obstructive or central origin, wherein the reference pressure is determined having regard to said evaluation result, and wherein the evaluation result indicative of whether or to what extent a prevailing or imminent breathing disorder is of obstructive or central origin is based solely on a variation in respiratory cycle-specific reference features obtained via differentiation.

31. The apparatus as set forth in claim 30, further comprising a respiratory gas line extending between the delivery device and a breathing mask.

32. An evaluation apparatus for evaluation of a series of measurement data which contains items of information indicative in respect of the pattern in respect of time of the breathing of a patient, comprising:

a signal processing device configured to generate, based on a variation in respiratory cycle-specific reference features obtained via differentiation, evaluation results indicative of whether or to what extent the measurement series contains sequences which are to be classified as a breathing disorder of obstructive or central origin, wherein the signal processing device is configured to generate the evaluation result based on the variation in respiratory cycle-specific reference features obtained directly via differentiation.

33. An evaluation apparatus as set forth in claim 32, further comprising a display configured to visualize the measurement series at least in portion-wise manner and to distinguish sequences of presumed disturbed breathing as sequences of obstructive or central origin.

34. A method of carrying out signal-processing consideration of a measurement signal related to the respiration activity of a person when matching pressure regulation in administering a breathable gas at a pressure level which at least in phase-wise manner is above ambient pressure, the method comprising:

generating evaluation results of the measurement signal, on a positive airway pressure (PAP) device, indicative of the respiratory gas flow, the evaluation results permitting classification between obstructive and central breathing disorders; and analyzing, on the PAP device, the number of local maxima and minima, the amplitude of the local maxima and minima, the sequence of the magnitude of the amplitudes of local maxima and minima, and the frequency in the sequence of local maxima and minima in considering the configuration of the curve shape.

35. A method of carrying out signal-processing consideration of a measurement signal related to the respiration activity of a person when matching pressure regulation in administering a breathable gas at a pressure level which at least in phase-wise manner is above ambient pressure, the method comprising:

generating evaluation results of the measurement signal, on a positive airway pressure (PAP) device, indicative of the respiratory gas flow, the evaluation results permitting classification between obstructive and central breathing disorders, wherein the signal processing further includes spectral consideration and consideration in respect of amplitude of a snoring signal, the signal processing being performed on the PAP device.

36. A method of carrying out signal-processing consideration of a measurement signal related to the respiration activity of a person when matching pressure regulation in administering a breathable gas at a pressure level which at least in phase-wise manner is above ambient pressure, the method comprising:

generating evaluation results of the measurement signal, on a positive airway pressure (PAP) device, indicative of the respiratory gas flow, the evaluation results permitting classification between obstructive and central breathing disorders, wherein said evaluation results are generated on the PAP device based on an evaluation procedure which gives information about at least one of the following: the nature of the upper respiratory tracts, at least for differentiating between central and obstructive apneas, the elastic properties of the upper respiratory tracts (including restoring modulus and/or modulus of elasticity), the location of an obstruction, the degree of severity of a sleep apnea, and the Pcrit-value.

37. A method of carrying out signal-processing consideration of a measurement signal related to the respiration activity of a person when matching pressure regulation in administering a breathable gas at a pressure level which at least in phase-wise manner is above ambient pressure, the method comprising:

generating evaluation results of the measurement signal on a positive airway pressure (PAP) device, the evaluation results permitting classification between obstructive and central breathing disorders and being indicative of the respiratory gas flow via differentiation, wherein the signal-processing consideration is carried out on the PAP device (1) based on consideration of a derivative taken at the beginning of the inspiration cycle or at the end of the inspiration cycle, and/or (2) based on consideration of a derivative taken at the beginning of the expiration cycle or at the end of the expiration cycle.

38. A method of carrying out signal-processing consideration of a measurement signal related to the respiration activity of a person when matching pressure regulation in administering a breathable gas at a pressure level which at least in phase-wise manner is above ambient pressure, the method comprising:

differentiating the measurement signal on a positive airway pressure (PAP) device to generate evaluation results indicative of the respiratory gas flow, the differentiating permitting classification between obstructive and central breathing disorders, wherein classification between obstructive and central breathing disorders is based on variables and/or mathematical operations consisting essentially of the differentiating.

* * * * *